United States Patent [19]

Eikenberry

[11] Patent Number: 4,547,460
[45] Date of Patent: * Oct. 15, 1985

[54] MULTIZONE ANALYTICAL ELEMENT AND METHOD FOR ANALYTE DETERMINATION

[75] Inventor: Jon N. Eikenberry, Rochester, N.Y.

[73] Assignee: Eastman Kodak Company, Rochester, N.Y.

[*] Notice: The portion of the term of this patent subsequent to Oct. 15, 2002 has been disclaimed.

[21] Appl. No.: 600,641

[22] Filed: Apr. 16, 1984

[51] Int. Cl.$^4$ .................. C12Q 1/32; C12Q 1/48; G01N 33/52

[52] U.S. Cl. .................................. 435/15; 422/56; 422/57; 435/26; 435/805; 436/170; 436/175

[58] Field of Search .................. 422/55–58; 436/169, 170, 175; 435/15, 16, 26, 805

[56] References Cited

U.S. PATENT DOCUMENTS

| | | |
|---|---|---|
| 3,014,810 | 12/1961 | Dybalski et al. |
| 3,816,262 | 6/1974 | Monte |
| 3,992,158 | 11/1976 | Przybylowicz et al. |
| 4,050,898 | 9/1977 | Goffe et al. |
| 4,069,017 | 1/1978 | Wu et al. |
| 4,153,668 | 5/1979 | Hill et al. |
| 4,292,272 | 9/1981 | Kitajima et al. ............ 422/56 X |
| 4,303,408 | 12/1981 | Kim et al. ............ 422/57 X |
| 4,329,425 | 5/1982 | Ricci et al. ............ 435/15 X |

FOREIGN PATENT DOCUMENTS 2085581 4/1982 United Kingdom .

Primary Examiner—Arnold Turk

Attorney, Agent, or Firm—J. Lanny Tucker

[57] ABSTRACT

A multizone analytical element for the determination of an analyte in an aqueous liquid comprises a registration zone and a porous spreading zone to receive and transport the aqueous liquid. The spreading zone contains a nonpolymeric quaternary ammonium compound represented by either of the structures:

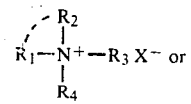

Ia.

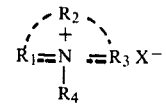

Ib.

wherein ═══ represents a single or double bond; $R_1$, $R_2$, $R_3$ and $R_4$ are independently alkyl; aryl; cycloalkyl; or alkaryl; provided that $R_1$, $R_2$, $R_3$ and $R_4$ together comprise at least 12 carbon atoms; or $R_1$ and $R_2$ taken together with the nitrogen atom, form a quaternary 5- to 16-membered heterocyclic ring; or $R_1$, $R_2$ and $R_3$ taken together with the nitrogen atom, form a quaternary 5- to 16-membered heterocyclic ring; and $X^-$ is a monovalent anion. This element is particularly useful for rate determinations of enzymes, such as alanine aminotransferase and aspartate aminotransferase, in liquids containing bilirubin or protein which may interfere with the accuracy of the assay.

21 Claims, No Drawings

MULTIZONE ANALYTICAL ELEMENT AND METHOD FOR ANALYTE DETERMINATION

RELATED APPLICATION

Reference is made to my copending and commonly assigned application U.S. Ser. No. 600,646, filed on even date herewith and entitled ANALYTICAL ELEMENT HAVING IMPROVED SPREADING ZONE AND METHOD OF USE.

FIELD OF THE INVENTION

This invention relates to a dry multizone element useful for the chemical analysis of water, foodstuffs and biological liquids. In particular, it relates to multizone elements which provide highly accurate analysis of liquids which may contain bilirubin or protein materials which can act as interferents in the analysis. This invention also relates to a method of using such elements for the determination of an analyte, such as a low level enzyme.

BACKGROUND OF THE INVENTION

Chemical analysis of water, foodstuffs like milk and biological fluids such as serum and urine is often desirable or necessary. Various analytical elements to facilitate such analyses are known. Generally, such elements include a reagent (hereinafter termed interactive composition), for a substance under analysis (hereinafter termed analyte). The interactive composition, upon contact with a liquid sample containing the analyte, effects a detectable change in response to the presence of the analyte. For example, such a detectable change can be the formation or disappearance (e.g. reduction) of a detectable species, e.g. a dye. Such a change can be determined as it occurs (i.e. a rate assay), or after a certain time (i.e. endpoint assay).

In the diagnostic clinical analysis of complex biological fluids, such as serum, whole blood, urine, etc., it is known that substances present in the patient sample other than the analyte being determined, can interfere with or bias the analytical results such that the end results are not in direct proportion to the concentration of the analyte. This interference is particularly harmful in analyses of analytes which are present in the sample at low concentrations (e.g. certain low level enzymes). Such interference is also particularly prominent when the analyte is determined using a rate assay versus an endpoint assay.

For example, in the analysis of two low level enzymes, aspartate aminotransferase (AST) and alanine aminotransferase (ALT), using conventional NADH-based interactive compositions, the rate of enzyme activity in a sample is determined by observing the rate of disappearance of NADH which can be spectrophotometrically measured at 340 nm. It has been found that the results of such AST and ALT analyses are adversely affected by the presence of bilirubin and proteins in the liquid test sample. In the presence of bilirubin, the results were positively biased away from the true analyte concentration. It was also observed that variations in total protein concentration altered the results such that AST and ALT were underestimated at low protein levels and overestimated at high protein levels.

Recently, much work has been directed toward developing dry analytical elements useful in diagnostic chemical analysis, where testing of biological fluids provide highly quantitative results quickly and conveniently. For example, U.S. Pat. No. 3,992,158 (issued Nov. 16, 1976 to Przybylowicz et al) describes integral analytical elements which are a significant advance in the clinical chemistry art. However, such elements need further modification to overcome the interference of bilirubin and protein noted above and to provide improved assay accuracy.

In U.S. Pat. No. 4,153,668 (issued May 8, 1979 to Hill et al), immobilized polymeric cationic materials are incorporated into the spreading layer of dry analytical elements in order to more uniformly disperse a liquid sample of a negatively-charged protein-bound or proteinaceous substance. This reference teaches that it is essential to the described advantage of uniform distribution of protein analyte that the cationic material be immobilized so that it cannot migrate throughout the element in order to assay for proteins. The purpose of incorporating the charged polymers is to uniformly disperse the liquid sample and to reduce a chromatographic effect. There is no teaching that the charged polymers remove interfering materials, such as bilirubin or proteins.

Other immobilized, positively charged polymeric materials are described in U.S. Pat. No. 4,069,017 (issued Jan. 17, 1978 to Wu et al). Such materials are used to mordant bilirubin in hydrophilic layers beneath a spreading layer in elements adapted for the analysis of bilirubin. It has been observed that such materials fail to consistently remove the effects of bilirubin or protein interference.

U.K. patent application No. 2,085,581 (published Apr. 28, 1982), teaches the use of tertiary amines in hydrophilic extraction layers of elements designed for the determination of bilirubin. Such amines apparently perform similarly to polymeric mordants in a separate extracting layer.

Nowhere does the art teach how one skilled in the clinical chemistry art can perform assays using dry elements for analytes other than bilirubin or proteins whereby the interfering effects of bilirubin or protein are avoided. Hence, there is a need in the art for a dry analytical element which is capable of providing highly accurate analyses of liquid samples and of avoiding the interfering effects of bilirubin or proteins in the liquid sample.

SUMMARY OF THE INVENTION

The present invention provides an improved dry analytical element which overcomes the interference by bilirubin and proteins observed in certain assays and which can be used to provide highly accurate analyte determinations. In particular, the elements of this invention have a porous spreading zone containing one or more compounds of a particular class of nonpolymeric positively charged compounds. The incorporation of this compound in the spreading zone substantially eliminates the adverse affect of bilirubin or protein, or both, in the analysis of aqueous liquids containing same. Analyte determinations made with the improved elements of this invention are especially accurate and advantageous for determination of analytes which are present in the test samples in very low concentrations. Such analytes include AST and ALT, as well as other enzymes commonly found in the human body.

It is surprising that the particular class of cationic compounds described herein provide the above-noted advantages because they are nonpolymeric and therefore, would be expected to migrate throughout the element. Generally, compound migration is not desirable because it adds to the unpredictability of the compound, the likelihood of adverse reactions and an overall reduction in the desired result. The positively charged polymers incorporated into elements adapted for assay of proteinaceous substances described in the Hill et al patent (noted hereinabove) are specifically immobilized in order to prevent their migration. Unexpectedly, however, the nonpolymeric compounds described hereinbelow substantially eliminate the effect of specific interferents, e.g. bilirubin or protein, on assays for other analytes.

Therefore, in accordance with this invention, a multizone analytical element for the determination of an analyte in an aqueous liquid comprises, in fluid contact,
a registration zone, and
a porous spreading zone containing a nonpolymeric quaternary ammonium compound represented by the structures:

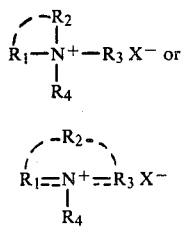

Ia.

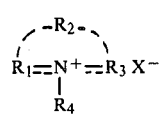

Ib.

wherein $\rlap{=}{-}$ represents a single or double bond;
$R_1$, $R_2$, $R_3$ and $R_4$ are independently alkyl of 1 to 30 carbon atoms; aryl of 6 to 14 carbon atoms; cycloalkyl of 5 to 20 carbon atoms; or alkaryl of 7 to 30 carbon atoms; provided that $R_1$, $R_2$, $R_3$ and $R_4$ together comprise at least 12 carbon atoms; or $R_1$ and $R_2$ taken together with the nitrogen atom, form a quaternary 5- to 16-membered heterocyclic ring and $R_3$ and $R_4$ are as defined above and comprise together at least 12 carbon atoms; or $R_1$, $R_2$ and $R_3$ taken together with the nitrogen atom, form a quaternary 5- to 16-membered heterocyclic ring and $R_4$ is as defined above and comprises at least 12 carbon atoms; and $X^-$ is a monovalent anion. The quaternary ammonium compound is present in the spreading zone in an amount effective to substantially eliminate the interfering effect of the bilirubin or protein interferent on the analyte determination.

In preferred embodiments, these elements also contain an interactive composition for the analyte.

This invention also provides a method for the determination of an analyte in an aqueous liquid containing bilirubin or a protein interferent using the element of this invention. This method comprises the steps of:
A. physically contacting a sample of the liquid containing the analyte together with an interactive composition for the analyte and the element described hereinabove to provide a detectable change in the element; and
B. measuring the detectable change.

DETAILED DESCRIPTION OF THE INVENTION

The improved assay accuracy obtained with this invention is achieved due to the incorporation in the porous spreading layer of one or more nonpolymeric quaternary ammonium compounds represented by the structures (Ia and b) given hereinbelow. These compounds have at least 12 carbon atoms. As used herein, the term "nonpolymeric" means that the compounds are not composed of repeating quaternary ammonium cationic moieties and generally have a molecular weight of less than about 4000, and preferably less than about 2000. Such a compound is present in the spreading zone in an amount of at least about 0.1, preferably from about 0.2 to about 3, and more preferably from about 0.5 to 1.5, g/m$^2$, although any amount which substantially improves assay accuracy or is effective to substantially eliminate the effect of the bilirubin or protein interferent on the analyte determination can be used. This amount varies with the amount of bilirubin or total protein in the liquid sample being assayed. As used herein, the phrase "substantially eliminate the effect" means that, with a given test sample, generally bias (defined hereinbelow) of the analyte determination is reduced to an absolute value of 12% or less.

Quaternary ammonium compounds which are useful in the practice of this invention can be represented by the structures:

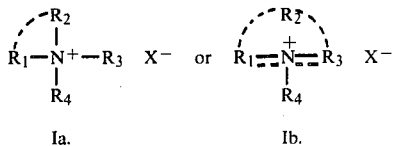

Ia.    Ib.

wherein $\rlap{=}{-}$ represents a single or double bond;
$R_1$, $R_2$, $R_3$ and $R_4$ are independently substituted or unsubstituted alkyl, preferably of 1 to 30 carbon atoms (e.g. methyl, ethyl, chloroethyl, isopropyl, decyl, dodecyl, 1-hydroxyethyl, alkyl groups substituted with a carbonamido moiety, e.g. propylene-NHCOC$_{17}$H$_{35}$, etc.); substituted or unsubstituted aryl, preferably of 6 to 14 carbon atoms in the aromatic backbone (e.g. phenyl, xylyl, naphthyl, p-methoxyphenyl, etc.); substituted or unsubstituted cycloalkyl, preferably of 5 to 20 carbon atoms in the carbocyclic ring (e.g. cyclopentyl, cyclohexyl, etc.); or substituted or unsubstituted alkaryl, preferably of 7 to 30 carbon atoms in the backbone (e.g. benzyl, 3-propylphenyl, etc.); provided that $R_1$, $R_2$, $R_3$ and $R_4$ together comprise at least 12 carbon atoms.

Alternatively, $R_1$ and $R_2$, taken together with the nitrogen atom, form a quaternary 5- to 16-membered heterocyclic ring, e.g. piperidinium, pyrrolidinium, morpholinium and the like to provide a heterocyclic amine having two pendant groups, $R_3$ and $R_4$, attached to the quaternary ammonium atom. This heterocyclic ring generally contains a total of 5 to 16 carbon atoms and heteroatoms (nitrogen, sulfur, oxygen and selenium atoms) in the ring backbone. The ring can be substituted if desired. $R_3$ and $R_4$ are independently alkyl, aryl, cycloalkyl or alkaryl as defined above but comprise together at least 12 carbon atoms.

In another alternative illustrated by structure Ib, $R_1$, $R_2$ and $R_3$, taken together with the nitrogen atom, can form a quaternary N-containing heterocyclic ring, e.g. quinolinium, pyridinium, pyrimidinium, acridinium, benzothiazolium, benzoxazolium, and the like to provide a heterocyclic amine having a single pendant group $R_4$. This heterocyclic ring generally contains a total of 5 to 16 carbon atoms and heteroatoms (nitrogen, sulfur, oxygen and selenium atoms) in the ring backbone. The ring can be substituted with any of a number of moieties known to one skilled in the art. In this heterocyclic compound, $R_4$ is alkyl, aryl, cycloalkyl or alkaryl as defined above but comprising at least 12 carbon atoms.

In this embodiment illustrated by structure Ib, the heterocyclic amine preferably is a 6- to 10-membered, quaternary heterocyclic ring (e.g. pyridinium, benzothiazolium, acridinium, etc.). Preferably, $R_4$ is alkyl (as defined above) of 12 to 30 carbon atoms.

$X^-$ is any suitable monovalent anion, such as halide, nitrate, phosphate, sulfate and the like.

In a more preferred embodiment, $R_1$ and $R_2$ are independently substituted or unsubstituted alkyl of 1 to 6 carbon atoms (methyl, ethyl, isopropyl, t-butyl, etc.); $R_3$ and $R_4$ are independently alkyl of 1 to 30 carbon atoms, aryl of 6 to 14 carbon atoms, or alkaryl of 7 to 30 carbon atoms, as defined hereinabove; provided that $R_1$, $R_2$, $R_3$ and $R_4$ together comprise at least 12 carbon atoms; or $R_1$, $R_2$ and $R_3$, taken together with the nitrogen atom, form a quaternary 5- to 16-membered heterocyclic ring and $R_4$ is alkyl comprising at least 12 carbon atoms; and $X^-$ is halide or nitrate.

In a most preferred embodiment, $R_1$ and $R_2$ are independently alkyl of 1 to 6 carbon atoms; $R_3$ and $R_4$ are independently alkyl of 1 to 30 carbon atoms; provided that $R_1$, $R_2$, $R_3$ and $R_4$ together comprise at least 12 carbon atoms; or $R_1$, $R_2$ and $R_3$, taken together with the nitrogen atom, form a quaternary 6- to 10-membered heterocyclic ring and $R_4$ is alkyl comprising at least 12 carbon atoms; and X is halide or nitrate. Compounds so defined for this most preferred embodiment are particularly useful in the practice of this invention because they substantially eliminate the adverse affect of both bilirubin and proteins, whereas some of the compounds defined by structures (Ia) and (Ib) substantially eliminate the adverse effect of bilirubin only.

The following list of useful quaternary ammonium compounds is not exhaustive of compounds useful in the practice of this invention, but it provides a representative sampling of useful compounds. Useful compounds include:

which is a mixture of compounds wherein R' is substituted or unsubstituted alkyl of 12, 14 or 16 carbon atoms.

The multizone elements of this invention comprise a porous spreading zone. This zone is often termed a spreading or metering zone in the art because of its ability to spread, meter or transport applied liquid samples rapidly therein. Preferably, the spreading zone has isotropic porosity. Isotropic porosity means that the zone is substantially porous to aqueous liquid in all directions within the zone. It will be understood that the degree of porosity can be variable within the zone. In the elements of this invention, it is useful to have a void volume of at least about 25 percent of the total zone volume, and void volumes of 50 to 95 percent may be desirable in certain instances. As can be appreciated, void volume within the zone can be controlled, for example, by the selection of constituent materials, or by varying the solvents or drying conditions during preparation.

The porous zone can be in any suitable location in the element. It can be a self-supporting matrix so that the zone along with a registration zone described hereinbelow comprise the entire element. Preferably, however, the zones of the element are carried on a suitable substrate (or support hereinafter) and the spreading zone is the outermost layer on that support so that the liquid sample to be assayed comes into contact with this porous zone before any other part of the element. For example, an element can comprise one or more zones or layers which perform functions other than spreading but which element has the described porous layer as an outermost spreading layer to bring a sample of an aqueous liquid into contact with those other zones or layers. Alternatively, the element can have one or more other spreading or metering zones, and the particular porous zone described herein can be between these zones or between the support and all of the other zones. In such embodiments, another spreading zone is the outermost zone in the element.

The spreading zone can be composed of any suitable porous material known in the art. Useful materials for porous spreading zones include the blush polymers and particulate materials described, for example, in U.S. Pat. No. 3,992,158 (noted hereinabove); the fibrous materials described in U.S. Pat. No. 4,292,272 (issued Sept. 29, 1981 to Kitajima et al); and the particulate structures described in U.S. Pat. No. 4,258,001 (issued Mar. 24, 1981 to Pierce et al), U.S. Pat. No. 4,430,436 (issued Feb. 7, 1984 to Koyama et al); and Japanese patent publication No. 57(1982)-101760. The blush polymer spreading materials are particularly useful in the elements of this invention.

The elements of this invention also contain a registration zone in fluid contact with the spreading zone. The term "fluid contact" means that fluids can pass between superposed regions of adjacent zones. Stated in another manner, fluid contact refers to the ability to transport components of a fluid between the zones in fluid contact. The registration zone is so named because it is generally in that zone that the detectable species resulting from interaction of the analyte with an interactive composition (defined hereinbelow) is "registered" or detected spectrophotometrically. However, this invention includes elements where the detectable species is detected in the registration zone as well as in other zones simultaneously. It is intended to encompass instances where the detectable species is detected throughout the element, or in other parts of the element besides the registration zone.

Such registration zone is generally composed of one or more hydrophilic synthetic or natural materials, e.g. gelatin, agarose, hydrophilic synthetic polymers such as polyacrylamides, etc. and others known in the art; surfactants and any other materials known to be useful therein.

The elements of this invention can also comprise one or more buffers present in one or more zones the cumulative effect of which is to maintain the element at a desired pH when the element is used in an assay. The particular pH desired and the amount of buffer used will vary with the assay, but are within the skill of an ordinary worker in the clinical chemistry art.

The elements of this invention can further include an interactive composition therein although the presence of such a composition is not required in the element for practice of this invention (e.g. it could be added in the liquid sample or as a separate sample). These compositions can be a single chemical compound or a combination of chemical compounds or reagents which can interact with the analyte, with a reaction decomposition product of the analyte, or with each other, upon contact with the analyte to produce a detectable change. Such interaction is meant to refer to chemical reactivity, catalytic activity as in the formation of an enzyme-substrate complex, antigen-antibody reactions and any other form of chemical or physical interaction that can produce or promote within the element, such as in a reagent or spreading zone, a change which is radiometrically detectable, that is by suitable measurement of light or any other energy form. For example, the change can be release of a preformed detectable species, the formation of a detectable species or the disappearance or reduction in amount of a detectable species. The change produced can be correlated to the amount of analyte in the liquid sample.

The particular interactive composition distributed within the element will depend on the analysis of choice. The composition useful for a given analysis would be within the skill of a worker in the clinical chemistry art. The elements of this invention can be adapted, for example, for the analysis of ground water, foodstuffs, and biological fluids, such as blood, plasma, serum, cerebral spinal fluid, urine and the like. Analyses of glucose, lactate, triglycerides, uric acid and enzymes, such as creatine kinase, amyiase, alkaline phosphatase, lactate dehydrogenase, alanine aminotransferase (ALT) and aspartate aminotransferase (AST) are but representative of the potential uses of the elements of this invention. The elements and method of this invention are particularly useful for determination of low level enzyme analytes (i.e. those generally present in a liquid at a concentration of $<100$ U/L) such as AST, ALT, isoenzymes of lactate dehydrogenase and $\gamma$-glutamyltransferase. It is also particularly useful for assays which are NADH (nicotinamide adenine dinucleotide)-based (i.e. based on the rate of disappearance of NADH).

In preferred embodiments of this invention, the element is used to determine AST or ALT. The interactive composition for AST elements can include, for example, in quantities known by one skilled in the art, aspartic acid or an equivalent L-aspartate, $\alpha$-ketoglutarate, NADH, lactate dehydrogenase, malate dehydrogenase and pyridoxal phosphate. Alternatively, other interactive compositions known for determining AST can be used.

An interactive composition useful in ALT elements includes, for example, in quantitites known by one skilled in the art, L-alanine, NADH, $\alpha$-ketoglutarate, lactate dehydrogenase and pyridoxal phosphate. Alternatively, other interactive compositions known for determining ALT can be used, if desired.

The interactive composition can be placed in any suitable location in the element of this invention, i.e. all within a single zone, or the components of the composition can be distributed among two or more zones in the element.

The dry analytical elements of this invention have at least one porous spreading zone, as described hereinabove. This zone can also be a spreading/reagent zone if it contains the interactive composition or some component thereof. This zone can be a self-supporting carrier matrix, but preferably it is carried on a separate support along with the registration zone. Such a support is preferably a film or sheet made of any suitable dimensionally stable, and preferably transparent (i.e. radiation transmissive) material which transmits electromagnetic radiation of a wavelength between about 200 and about 900 nm. Useful support materials include polystyrene, polyesters [e.g. poly(ethylene terephthalate)], polycarbonates, cellulose esters, etc.

The element can have one or more other zones besides the spreading and registration zones already described (including spreading, reagent, subbing, buffer, reflective, barrier, etc. zones), some or all of which can contain reagents. These zones are in fluid contact with each other as defined hereinabove. Preferably, the zones are separate coated layers, although one or more zones can be in a single layer, or one or more separate layers can be in a single zone, of an element. Dry element formats and materials are known in the art and described for example in U.S. Pat. Nos. 3,992,159 (noted hereinabove); 4,042,335 (issued Aug. 16, 1977 to Clément); 4,144,306 (issued Mar. 13, 1979 to Figueras); 4,132,528 (issued Jan. 2, 1979 to Eikenberry et al); 4,258,001, 4,430,436 and 4,292,272 (each noted hereinabove); and Japanese patent publication No. 57(1982)-101760 (noted hereinabove); and U.S. Pat. No. 4,450,232 (issued May 22, 1984 to Sanford et al.).

Particularly useful elements for the determination of the transferases, AST and ALT, are illustrated in the examples hereinbelow.

The analytical method of this invention can be automated or manual. In general, an analyte in an aqueous liquid is determined by taking an element from a supply roll, slide packet or other source and physically contacting it with a sample of the liquid. Such contact can be accomplished in any suitable manner, e.g. dipping or immersing the element into the sample or, preferably, by spotting the element by hand or machine with a drop (e.g. about 1–20 μL) of the sample by pipette or another suitable dispensing means.

After sample application, the element is exposed to any conditioning, such as incubation, heating or the like, that may be desirable to quicken or otherwise facilitate obtaining any test result. The interactive composition will chemically react with any analyte present in the sample and produce a detectable change (as described hereinabove) which can be measured at an endpoint or as a rate change with suitable detection equipment and techniques. Such equipment includes conventional reflection, transmission or fluorescence spectrophotometers which are well known in the art.

In a preferred embodiment of this invention, a serum sample is physically contacted with an element adapted to determine AST or ALT using NADH-based chemistry. After suitable incubation, the rate of disappearance of NADH is measured with a suitable spectrophotometer. This rate of change can be correlated to the amount of AST or ALT in the serum sample.

The following examples illustrate the practice of this invention. In preparing the dry analytical elements, the components were obtained from the following sources: polyurethane resin (Estane TM 5715) from B. F. Goodrich (Cleveland, Ohio); Triton TM 405 surfactant from Rohm & Haas (Philadelphia, Pa.); dicocodimethyl ammonium chloride (Arquad TM 2C-75) from Armak Industries (Chicago, Ill.); sodium α-ketoglutarate from Sigma Chemical (St. Lous, Mo.); sodium aspartate from ICN Nutritional Biochemicals (Clevelant, Ohio); conjugated bilirubin from U.S. Biochemical Corp. (Cleveland, Ohio); lactate dehydrogenase, malate dehydrogenase and pyridoxal-5-phosphate from Boehringer Mannheim (Indianapolis, Ind.); NADH from P-L Biochemicals (Milwaukee, Wis.); stearyldimethylbenzyl ammonium chloride from Onyx Chemical Co. (Jersey City, N.J.); Cyastat SN TM from American Cyanamide (Wayne, N.J.); and the remainder from Eastman Organic Chemicals (Rochester, N.Y.) or from in-house sources.

In the examples, a bias determination was made by spotting a 10 μL aliquot of an aqueous test liquid onto the spreading layer of the multilayer element. The concentration of analyte (e.g. AST or ALT) in the aqueous test liquid was then determined by recording the rate of decrease in absorbance of NADH at 340 nm using a conventional reflectometer and the procedure described by Fitzsimmons in Clin. Chem., 29 1211(1983). Test samples of pooled human serum were then spiked with either unconjugated bilirubin, conjugated bilirubin, a mixture of both or total protein. The spiked samples were then assayed for AST or ALT concentration in a similar fashion, and any resulting bias was determined as the difference between the analyte value in the unspiked test sample and the analyte value of the spiked test sample. The bias is an indication of the accuracy of the assay. Acceptable bias is ±12% (i.e. an absolute value of 12 or less), but the closer the bias is to 0, the more accurate the assay. The elements of this invention exhibit improved accuracy as evidenced by a reduction in the absolute value of the % bias either in the presence of bilirubin, total protein or both. In some elements, the accuracy improvement is seen in the presence of bilirubin alone. In other and most preferred elements, the improvement is seen in the presence of both bilirubin and total protein.

EXAMPLES 1–3

AST Analytical Elements

Multilayer analytical elements for the determination of aspartate aminotransferase were prepared having the format and components shown hereinbelow. A Control element was similarly prepared except the quaternary ammonium compound was omitted from the spreading-/reagent layer.

| | | |
|---|---|---|
| Spreading/ Reagent Layer | Barium sulfate | 25–250 g/m$^2$ |
| | Cellulose acetate | 2.5–25 g/m$^2$ |
| | Estane TM 5715 polyurethane | 0.5–5 g/m$^2$ |
| | Triton TM X-405 surfactant | 0.6–6 g/m$^2$ |
| | Sodium α-ketoglutarate | 0.06–0.6 g/m$^2$ |
| | Sodium aspartate | 1.5–15 g/m$^2$ |
| | Quaternary ammonium compound* | 0.1–3 g/m$^2$ |
| Subbing Layer | Poly(vinyl pyrrolidone) | 0.15–1.5 g/m$^2$ |
| Registration Layer | Gelatin (hardened) | 3–30 g/m$^2$ |
| | Triton TM X-405 surfactant | 0.2–2 g/m$^2$ |
| | Tris(hydroxymethyl)amino methane buffer (pH 7.8) | 1.5–15 g/m$^2$ |
| | Lactate dehydrogenase | 300–3000 U/m$^2$ |
| | Malate dehydrogenase | 300–3000 U/m$^2$ |
| | NADH | 0.1–1 g/m$^2$ |
| | Pyridoxal-5-phosphate | 0.05–0.5 g/m$^2$ |
| | Poly(ethylene terephthalate) Support | |

*Example 1 Hexadecylpyridinium bromide
Example 2 Hexadecyltrimethyl ammonium bromide
Example 3 Nonyltrimethyl ammonium bromide Determinations of AST were made for samples of each element using the procedure described hereinabove and samples of either pooled human serum, pooled human serum containing bilirubin conjugate or unconjugated bilirubin, or pooled human serum containing 3% or 10% total protein. These levels of total protein were chosen because the accuracy of the assay is adversely affected most noticeably at either low (about 3%) or high (about 10%) levels, and less so in between. The bias of each AST determination was then calculated in a conventional manner. The results of the bias calculations are shown in Table I hereinbelow.

It can be seen from these data that hexadecylpyridinium bromide in Element 1 significantly improved the accuracy of the assay of test samples containing either bilirubin or total protein (both low and high levels). The absolute value of the % bias has been significantly reduced in all cases. The quaternary ammonium compounds in Examples 2 and 3 improved assay accuracy significantly of samples containing bilirubin only.

TABLE I

| Element | % Bias with Bilirubin | | % Bias with Total Protein | |
|---|---|---|---|---|
| | unconjugated | conjugated | 3% | 10% |
| Control A | −15 | −15 | −6 | +42 |
| Example 1 | +4 | −6 | +1 | +3 |
| Example 2 | +11 | +8 | +9 | +23 |
| Example 3 | −8 | −2 | −2 | +27 |

EXAMPLE 4

AST Analytical Element

A multilayer analytical element was prepared as described in Examples 1-3, except that Ammonyx TM - 4002 was used as the quaternary ammonium compound in the spreading/reagent layer. A Control element with such compound omitted was also prepared.

Determinations of AST were made by assaying test samples containing either bilirubin (mixture of both conjugated and unconjugated forms) or total protein (3% or 10% level). The bias of each determination was calculated and the biases are shown in Table II hereinbelow. The element prepared according to this invention containing the quaternary ammonium compound exhibited improved accuracy in the assay of test samples containing bilirubin.

TABLE II

| Element | % Bias with Bilirubin (mix of conjugated and unconjugated) | % Bias with Total Protein | |
|---|---|---|---|
| | | 3% | 10% |
| Control B | −29 | −10 | +35 |
| Example 4 | −3 | −21 | +16 |

EXAMPLE 5

AST Analytical Element

A multilayer analytical element was prepared as described in Examples 1-3, except dicocodimethyl ammonium chloride (Arquad TM 2C-75) was used as the quaternary ammonium compound in the spreading layer. A Control element with such compound omitted was also prepared.

Determinations of AST were made by assaying test samples containing either bilirubin (mixture of unconjugated and conjugated forms) or total protein (3% or 10% level). The bias of each determination was calculated and the biases are shown in Table III hereinbelow. These results indicate that the element prepared according to this invention containing the quaternary ammonium compound exhibited significant improvement in accuracy with test samples containing either bilirubin or total protein.

TABLE III

| Element | % Bias with Bilirubin | % Bias with Total Protein | |
|---|---|---|---|
| | | 3% | 10% |
| Control C | −36 | 0 | +27 |
| Example 5 | −5 | −8 | +6 |

EXAMPLES 6-7

ALT Analytical Elements

Multilayer analytical elements for the determination of alanine aminotransferase were prepared as described in Examples 1—3 except that L-alanine (2–20 g/m$^2$) was used in place of sodium aspartate in the spreading/reagent layer and malate dehydrogenase was omitted from the registration layer. Examples 6 and 7 contained hexadecylpyridinium bromide and benzyltriethyl ammonium chloride in the spreading/reagent layer, respectively. A Control element was similarly prepared but with the quaternary ammonium compound omitted.

Determinations of ALT in test samples containing either bilirubin (mixture of conjugated and unconjugated forms) or total protein (3% and 10% level) were made. The bias of each determination was calculated and the results are shown in Table IV hereinbelow. Both Examples 6 and 7 exhibited significant improvement in accuracy in the assay done in the presence of bilirubin. The bias in the presence of total protein was improved in some cases, but not consistently.

TABLE IV

| Element | % Bias with Bilirubin | | % Bias with Total Protein | |
|---|---|---|---|---|
| | unconjugated | conjugated | 3% | 10% |
| Control D | −16 | −6 | −8 | +26 |
| Example 6 | −7 | −5 | −7 | +14 |
| Example 7 | 0 | 0 | +130 | +7 |

EXAMPLE 8

ALT Analytical Element

A multilayer analytical element was prepared as described in Examples 6 and 7 except that benzyldimethylphenyl ammonium chloride was incorporated in the spreading/reagent layer. A Control element with the quaternary ammonium compound omitted was similarly prepared.

Determinations of ALT with test samples containing either bilirubin (mixture of conjugated and unconjugated forms) or total protein (3% and 10% level) were made. The bias of each determination was calculated and the results, shown in Table V hereinbelow, indicate that the element of this invention exhibited improved accuracy in the assay of ALT where bilirubin was present but not where total protein was present.

TABLE V

| Element | % Bias with Bilirubin | % Bias with Total Protein | |
|---|---|---|---|
| | | 3% | 10% |
| Control E | −11 | +30 | −9 |
| Example 8 | +3 | +135 | −16 |

EXAMPLE 9

ALT Analytical Element

A multilayer analytical element was prepared as described in Examples 6 and 7 except that dodecyltrimethyl ammonium chloride was incorporated in the spreading/reagent layer. A Control element with the quaternary ammonium compound omitted was similarly prepared.

Determinations of ALT with test samples containing either bilirubin (mixture of conjugated and unconjugated forms) or total protein (3% and 10% level) were made. The bias of each determination was calculated and the results, shown in Table V hereinbelow, indicate that the element of this invention exhibited significant improved accuracy in the assay of ALT where bilirubin was present but not where total protein was present.

TABLE VI

| Element | % Bias with Bilirubin | % Bias with Total Protein | |
|---|---|---|---|
| | | 3% | 10% |
| Control F | −57 | +96 | −31 |
| Example 9 | −9 | +75 | −40 |

EXAMPLE 10

AST Analytical Element Using Hexadecylpyridinium Bromide

A multilayer analytical element for the determination of aspartate aminotransferase (AST) was prepared having the format and components described in Examples 1-3 hereinabove. Hexadecylpyridinium bromide (0.1–3 g/m$^2$) was incorporated in the spreading/reagent layer of the element prepared according to this invention. Control elements containing polymeric quaternary mordants in place of hexadecylpyridinium bromide, or omitting all quaternary ammonium compounds, were similarly prepared.

Determinations of AST were made with samples of each element using the procedure described hereinabove and samples of pooled human serum, pooled human serum containing bilirubin (both conjugated and unconjugated forms), or pooled human serum containing 3% or 10% total protein. The bias of each AST determination was then calculated in a conventional manner. The results of the bias calculations are shown in Table VII hereinbelow.

It can be seen from these data that only the element of this invention exhibited improved accuracy in the assay of all test samples.

TABLE VII

| Element | % Bias with Bilirubin | | % Bias with Total Protein | |
|---|---|---|---|---|
| | unconjugated | conjugated | 3% | 10% |
| Control G* | −15 | −15 | −6 | +42 |
| Control H** | −6 | −3 | −13 | +3 |
| Control I*** | 0 | 2 | −13 | +19 |
| Example 10 | 4 | −6 | +1 | +3 |

*No quaternary ammonium compound in this element.
**The spreading/reagent layer contained 0.1-3 g/m$^2$ of poly[styrene-co-N,N,N—trimethyl-N—vinyl-benzylammonium chloride].
***The spreading/reagent layer contained 0.1-3 g/m$^2$ of poly[styrene-co-N—vinylbenzyl-N,N—dimethylbenzylammonium chloride-co-divinylbenzene].

EXAMPLE 11

ALT Analytical Element Using Hexadecylpyridinium Bromide

A multilayer analytical element for the determination of alanine aminotransferase (ALT) was prepared having the format and components described in Examples 6-7 hereinabove. Hexadecylpyridinium bromide (0.1–3 g/m$^2$) was incorporated in the spreading/reagent layer of the element prepared according to this invention. Control elements containing polymeric quaternary mordants in place of hexadecylpyridinium bromide, or omitting all quaternary ammonium compounds, were similarly prepared.

Determinations of ALT were made with samples of each element using the procedure described hereinabove and test samples of pooled human serum containing bilirubin (conjugated or unconjugated forms, or both) or total protein (3% or 10% level). The bias of each ALT determination was then calculated in a conventional manner. The results of the bias calculations are shown in Table VIII hereinbelow.

It can be seen from these data that only the element of this invention exhibited substantially improved accuracy in the assay.

TABLE VIII

| Element | % Bias with Bilirubin | | % Bias with Total Protein | |
|---|---|---|---|---|
| | unconjugated | conjugated | 3% | 10% |
| Control J* | −16 | −6 | −8 | +26 |
| Control K** | −18 | not tested | +29 | +49 |
| Control L*** | not tested | −11 | −16 | +19 |
| Example 11 | −7 | −5 | −7 | +14 |

*No quaternary ammonium compound in this element.
**The spreading/reagent contained 0.1-3 g/m$^2$ of poly[N,N,N—trimethyl-N—vinylbenzylammonium chloride-co-ethylene dimethacrylate].
***The spreading/reagent contained 0.1-3 g/m$^2$ of poly[N—benzyl-N,N—dimethyl-N—vinylbenzylammonium chloride-co-N,N—dimethyl-N—(2-morpholinoethyl)-N—vinylbenzylammonium chloride].

The invention has been described in detail with particular reference to preferred embodiments thereof, but it will be understood that variations and modifications can be effected within the spirit and scope of the invention.

I claim:

1. A multizone analytical element for the determination of an analyte which determination is substantially unaffected by the presence of bilirubin, said element comprising, in fluid contact,
    a registration zone, and
    a porous spreading zone containing a nonpolymeric quaternary ammonium compound represented by the structures:

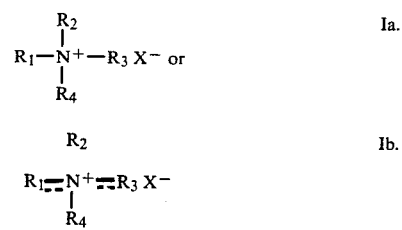

wherein $=$ represents a single or double bond;
$R_1$, $R_2$, $R_3$ and $R_4$ are independently alkyl of 1 to 30 carbon atoms; aryl of 6 to 14 carbon atoms; cycloalkyl of 5 to 20 carbon atoms; or alkaryl of 7 to 30 carbon atoms; provided that $R_1$, $R_2$, $R_3$ and $R_4$ together comprise at least 12 carbon atoms; or $R_1$ and $R_2$ taken together with the nitrogen atom, form a quaternary 5- to 16-membered heterocyclic ring and $R_3$ and $R_4$ are as defined above and comprise together at least 12 carbon atoms; or $R_1$, $R_2$ and $R_3$ taken together with the nitrogen atom, form a quaternary 5- to 16-membered heterocyclic ring and $R_4$ is as defined above and comprises at least 12 carbon atoms; and $X^-$ is a monovalent anion;
said quaternary ammonium compound being present in said spreading zone in an amount effective to substantially eliminate interference caused by bilirubin on said analyte determination.

2. The element of claim 1 wherein said quaternary ammonium compound is present in an amount of at least about 0.1 mg/m².

3. The element of claim 1 wherein $R_1$ and $R_2$ are independently alkyl of 1 to 6 carbon atoms; $R_3$ and $R_4$ are independently alkyl of 1 to 30 carbon atoms, aryl of 6 to 14 carbon atoms, or alkaryl of 7 to 30 carbon atoms; provided that $R_1$, $R_2$, $R_3$ and $R_4$ together comprise at least 12 carbon atoms; or $R_1$, $R_2$ and $R_3$, taken together with the nitrogen atom, form a quaternary 5- to 16-membered heterocyclic ring and $R_4$ is alkyl comprising at least 12 carbon atoms; and $X^-$ is halide or nitrate.

4. The element of claim 3 wherein $R_1$ and $R_2$ are independently alkyl of 1 to 6 carbon atoms; $R_3$ and $R_4$ are independently alkyl of 1 to 30 carbon atoms, provided that $R_1$, $R_2$, $R_3$ and $R_4$ together comprise at least 12 carbon atoms; or $R_1$, $R_2$ and $R_3$, taken together with the nitrogen atom, form a quaternary 6- to 10-membered heterocyclic ring and $R_4$ is alkyl comprising at least 12 carbon atoms, said quaternary ammonium compound being present in an amount effective to substantially eliminate interfering effects of both bilirubin and protein on said analyte determination.

5. The element of claim 4 wherein said quaternary ammonium compound is a heterocyclic amine represented by the structure (Ib) wherein $R_1$, $R_2$ and $R_3$, taken together with the nitrogen atom, complete a 6- to 10-membered quaternary heterocyclic ring.

6. The element of claim 1 wherein said quaternary ammonium compound is selected from the group consisting of:

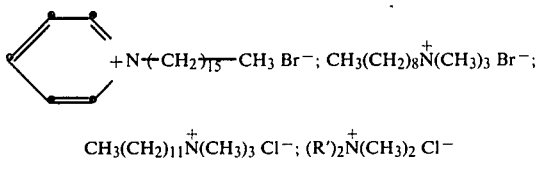

wherein R' is alkyl of 12, 14 or 16 carbon atoms;

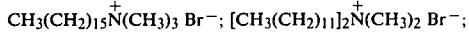

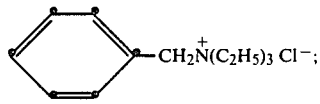

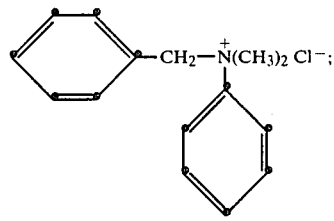

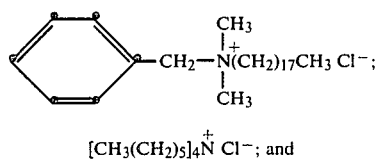

$[CH_3(CH_2)_5]_4\overset{+}{N}$ $Cl^-$; and

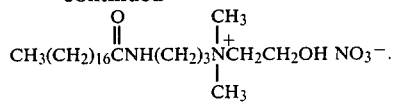

7. The element of claim 1 containing an interactive composition for said analyte.

8. A multizone analytical element for the determination of an analyte which determination is substantially unaffected by the presence of bilirubin, said element comprising a support having thereon, in order and fluid contact, a registration zone, and a porous spreading zone containing a nonpolymeric quaternary ammonium compound represented by the structures:

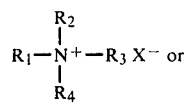 Ia.

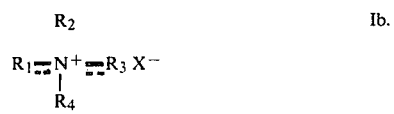 Ib.

wherein === represents a signal or double bond;

$R_1$, $R_2$, $R_3$ and $R_4$ are independently alkyl of 1 to 30 carbon atoms; aryl of 6 to 14 carbon atoms; cycloalkyl of 5 to 20 carbon atoms; or alkaryl of 7 to 30 carbon atoms; provided that $R_1$, $R_2$, $R_3$ and $R_4$ together comprise at least 12 carbon atoms; or $R_1$ and $R_2$ taken together with the nitrogen atom, form a quaternary 5- to 16-membered heterocyclic ring and $R_3$ and $R_4$ are as defined above and comprise together at least 12 carbon atoms; or $R_1$, $R_2$ and $R_3$ taken together with the nitrogen atom, form a quaternary 5- to 16-membered heterocyclic ring and $R_4$ is as defined above and comprises at least 12 carbon atoms; and $X^-$ is a monovalent anion;

said quaternary ammonium compound being present in said spreading zone in an amount effective to substantially eliminate interference caused by of bilirubin on said analyte determination;

and said element containing an interactive composition for an analyte to be determined.

9. The element of claim 8 wherein said interactive composition is a NADH-based reagent composition.

10. A multilayer analytical element for the rate determination of an enzyme in an aqueous liquid, said element comprising a support having thereon, in order and fluid contact, a registration layer containing at least one component of said interactive composition, and an isotropically porous spreading layer to receive and transport said aqueous liquid, said spreading layer containing a nonpolymeric quaternary ammonium compound represented by the structures:

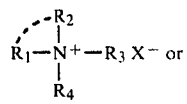 Ia.

-continued

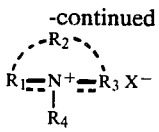
Ib.

wherein ⇌ represents a single or double bond;
$R_1$, $R_2$, $R_3$ and $R_4$ are independently alkyl of 1 to 30 carbon atoms; aryl of 6 to 14 carbon atoms; cycloalkyl of 5 to 20 carbon atoms; or alkaryl of 7 to 30 carbon atoms; provided that $R_1$, $R_2$, $R_3$ and $R_4$ together comprise at least 12 carbon atoms; or $R_1$ and $R_2$ taken together with the nitrogen atom, form a quaternary 5- to 16-membered heterocyclic ring and $R_3$ and $R_4$ are as defined above and comprise together at least 12 carbon atoms; or $R_1$, $R_2$ and $R_3$ taken together with the nitrogen atom, form a quaternary 5- to 16-membered heterocyclic ring and $R_4$ is as defined above and comprises at least 12 carbon atoms; and $X^-$ is a monovalent anion;
said quaternary ammonium compound being present in said spreading zone in an amount of at least about 0.1 mg/m²;
and said element containing a NADH-based reagent composition which can interact with an enzyme to be determined.

11. The element of claim 10 wherein said analyte is aspartate aminotransferase and said interactive composition comprises NADH, L-aspartate, α-ketoglutarate, lactate dehydrogenase, malate dehydrogenase and pyridoxal phosphate, or said analyte is alanine aminotransferase and said interactive composition comprises NADH, L-alanine, α-ketoglutarate, lactate dehydrogenase and pyridoxal phosphate.

12. The element of claim 10 wherein said spreading layer comprises a blush polymer.

13. The element of claim 10 wherein $R_1$ and $R_2$ are independently alkyl of 1 to 6 carbon atoms; $R_3$ and $R_4$ are independently alkyl of 1 to 30 carbon atoms, aryl of 6 to 14 carbon atoms, or alkaryl of 7 to 30 carbon atoms; provided that $R_1$, $R_2$, $R_3$ and $R_4$ together comprise at least 12 carbon atoms; or $R_1$, $R_2$ and $R_3$, taken together with the nitrogen atom, form a quaternary 5- to 16-membered heterocyclic ring and $R_4$ is alkyl comprising at least 12 carbon atoms; and $X^-$ is halide or nitrate.

14. The element of claim 13 wherein $R_1$ and $R_2$ are independently alkyl of 1 to 6 carbon atoms; $R_3$ and $R_4$ are independently alkyl of 1 to 30 carbon atoms, provided that $R_1$, $R_2$, $R_3$ and $R_4$ together comprise at least 12 carbon atoms; or $R_1$, $R_2$ and $R_3$, taken together with the nitrogen atom, form a quaternary 6- to 10-membered heterocyclic ring and $R_4$ is alkyl comprising at least 12 carbon atoms.

15. The element of claim 14 wherein said quaternary ammonium compound is

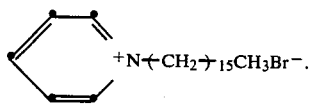

16. A method for the determination of an analyte in an aqueous liquid, which determination is substantially unaffected by the presence of bilirubin, said method comprising the steps of:
A. physically contacting a sample of said liquid containing the analyte together with an interactive composition for said analyte and a multizone analytical element to provide a detectable change in said element, said element comprising, in fluid contact,
a registration zone, and
a porous spreading zone to receive and transport an applied sample of said aqueous liquid, said spreading zone containing a nonpolymeric quaternary ammonium compound represented by the structures:

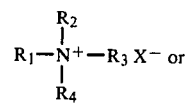

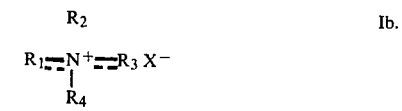

wherein ⇌ represents a single or double bond;
$R_1$, $R_2$, $R_3$ and $R_4$ are independently alkyl of 1 to 30 carbon atoms; aryl of 6 to 14 carbon atoms; cycloalkyl of 5 to 20 carbon atoms; or alkaryl of 7 to 30 carbon atoms; provided that $R_1$, $R_2$, $R_3$ and $R_4$ together comprise at least 12 carbon atoms; or $R_1$ and $R_2$ taken together with the nitrogen atom, form a quaternary 5- to 16-membered heterocyclic ring and $R_3$ and $R_4$ are as defined above and comprise together at least 12 carbon atoms; or $R_1$, $R_2$ and $R_3$ taken together with the nitrogen atom, form a quaternary 5- to 16-membered heterocyclic ring and $R_4$ is as defined aove and comprises at least 12 carbon atoms; and $X^-$ is a monovalent anion;
said quaternary ammonium compound being present in said spreading zone in an amount effective to substantially eliminate interference caused by of bilirubin on said analyte determination; and
B. measuring said detectable change.

17. The method of claim 16 wherein said detectable change is in the rate of formation of a detectable species.

18. The method of claim 16 wherein said detectable change is in the rate of disappearance of a detectable species.

19. The method of claim 16 wherein said interactive composition is incorporated within said analytical element.

20. The method of claim 16 wherein said analyte is aspartate aminotransferase and said interactive composition comprises NADH, L-aspartate, α-ketoglutarate, lactate dehydrogenase, malate dehydrogenase and pyridoxal phosphate; or said analyte is alanine aminotransferase and said interactive composition comprises NADH, L-alanine, α-ketoglutarate, lactate dehydrogenase and pyridoxal phosphate.

21. The method of claim 16 wherein $R_1$ and $R_2$ are independently alkyl of 1 to 6 carbon atoms; $R_3$ and $R_4$ are independently alkyl of 1 to 30 carbon atoms, provided that $R_1$, $R_2$, $R_3$ and $R_4$ together comprise at least 12 carbon atoms; or $R_1$, $R_2$ and $R_3$, taken together with the nitrogen atom, form a quaternary 6- to 10-membered heterocyclic ring and $R_4$ is alkyl comprising at least 12 carbon atoms, said quaternary ammonium compound being present in an amount effective to substantially eliminate interfering effects of both bilirubin and protein on said analyte determination.

* * * * *